United States Patent [19]

Kobayashi et al.

[11] 3,971,820

[45] July 27, 1976

[54] PROCESS FOR THE PRODUCTION OF DIAMINOMALEONITRILE

[75] Inventors: Tatsumi Kobayashi, Kurashiki; Eiji Nishiwaki, Arai; Shigeharu Yamazoe, Tokyo; Mitsuyuki Hoshino, Urawa; Sadafumi Yoshino; Katsunori Mikuma, both of Kurashiki, all of Japan

[73] Assignee: Nippon Soda Company Limited, Tokyo, Japan

[22] Filed: Nov. 25, 1974

[21] Appl. No.: 526,631

Related U.S. Application Data

[63] Continuation-in-part of Ser. No. 400,858, Sept. 26, 1973.

[30] Foreign Application Priority Data

Nov. 30, 1973 Japan............................. 48-133596

[52] U.S. Cl........................................ 260/465.5 R
[51] Int. Cl.$^2$............... C07C 120/00; C07C 121/30
[58] Field of Search............................ 260/465.5 R

[56] References Cited

UNITED STATES PATENTS

| 3,701,797 | 10/1972 | Okada et al................. 260/465.5 R |
| 3,714,222 | 1/1973 | Hartter........................ 260/465.5 R |

*Primary Examiner*—Joseph P. Brust
*Attorney, Agent, or Firm*—George B. Oujevolk

[57] ABSTRACT

A process for tetramerizing hydrogen cyanide to diaminomaleonitrile, wherein hydrogen cyanide is polymerized in an organic solvent in the presence of a basic catalyst and a cocatalyst of the group consisting of organic mercaptans and organic disulfides.

11 Claims, No Drawings

PROCESS FOR THE PRODUCTION OF DIAMINOMALEONITRILE

CROSS-REFERENCE TO RELATED APPLICATION

This application is a continuation-in-part application of co-pending U.S. application Ser. No. 400,858, filed on Sept. 26, 1973.

BACKGROUND OF THE INVENTION

This invention relates to a process for producing diaminomaleonitrile, tetramer of hydrogen cyanide. Diaminomaleonitrile is a useful chemical product which is used as a raw material in the chemical industry for various organic materials, especially as an intermediate for synthesis of glycine, guanine, ademine, 4-aminoimidazole-5-carboxamide or the like.

German Disclosure Patent No. 2022243 discloses a process for producing diaminomaleonitrile wherein hydrogen cyanide is polymerized in a polar aprotic solvent, i.e. dimethyl sulfoxide and dimethyl formamide, in the presence of a basic catalyst such as NaCN, KCN, NaOH and $(C_2H_5)_3N$, maintaining the reaction mixture at a PH value of $10\pm1$, and thereby diaminomaleonitrile is obtained with a yield of 37 to 64%.

According to Japanese Disclosure Patent No. 2917/1971, diaminomaleonitrile is obtained with a yield of 16 to 63%, by polymerizing hydrogen cyanide at a temperature ranging from about $-40°C$ to $25°C$ in the presence of a basic catalyst such as trimethylamine, and at least one cocatalyst selected from the group consisting of dicyan and diiminosuccinonitrile.

According to Japanese Disclosure Patent No. 64021/1973, diaminomaleonitrile is obtained with a yield of 41 to 55.7% by polymerizing hydrogen cyanide employing saturated aliphatic mononitrile as a solvent in the presence of a basic catalyst.

The above-mentioned processes produce the desired compound with a low yield, so that the said compound, i.e. diaminomaleonitrile is expensive and useful chemicals such as glycine, guanine, ademine and 4-aminoimidazole-5-carboxamide which are synthesized from the said diaminomaleonitrile are also expensive. Consequently, those processes are economically unattractive.

A condition for producing diaminomaleonitrile from hydrogen cyanide with a high yield is to accelerate the velocity of converting hydrogen cyanide into diaminomaleonitrile and simultaneously to control the secondary reaction converting hydrogen cyanide into a high polymer.

The inventors scrutinized those conventional economically poor processes for producing diaminomaleonitrile and carried out the various types of research so as to find a method for improving those drawbacks.

As a result of the research, the inventors found that diaminomaleonitrile is obtained with a surprising high yield in a short reaction time by using organic mercaptans or organic disulfides as a catalyst when carrying out the polymerization reaction of hydrogen cyanide in a solvent in the presence of a basic catalyst.

It is the object of the invention to overcome the aforementioned problems and disadvantages and provide an improved process for producing diaminomaleonitrile.

Other and further objects, features and advantages of the invention will appear more fully from the following description.

DETAILED DESCRIPTION OF THE INVENTION

The process of the invention is carried out by tetramerizing hydrogen cyanide in an organic solvent in the presence of a basic catalyst and a cocatalyst selected from the group consisting of organic mercaptans and organic disulfides.

The organic mercaptans usable in the invention include aliphatic, aromatic, alicyclic and heterocyclic compound containing at least one —SH group.

Aliphatic mercaptans include alkyl mercaptans containing 1 to 8 of carbon atoms, preferably n-alkyl mercaptans. Aromatic mercaptans include aryl and aralkyl mercaptans, and these mercaptans having at least one substituent of halogen and lower alkyl which is preferably methyl or ethyl, for example, thiophenol, thionaphthol, benzylthiol, thiocresol, chlorothiophenol and thiocatechol. Alicyclic and heterocyclic mercaptans are, for example, cyclopentyl mercaptan, cyclohexyl mercaptan, 1,1-cyclohexyldithiol, 2mercaptobenzothiazole and 3-mercapto-5-methyl-1,2,4-triazole.

The organic disulfides usable in the invention include aliphatic, aromatic, alicyclic and heterocyclic compounds containing the bond of —S—S—, for example, dialkyl disulfides wherein alkyl is lower alkyl containing 1 to 8 carbon atoms, preferably 1 to 2, diaryl disulfides and diaralkyl disulfides and these disulfide having at least one substituent of halogen and lower alkyl which is preferably methyl or ethyl, i.e., diphenyl disulfide, dinaphthyl disulfide, dibenzyl disulfide, dicresol disulfide, dichlorodiphenyl disulfide, dicyclopentyl disulfide, dicyclohexyl disulfide, diimidazole disulfide, trimethylene disulfide, 1,2-dithiole-3-thion, benzo-1,2-dithiole-3-thion and benzo-1,2-dithiole-3-on.

In the industrial viewpoint, the preferable cocatalysts are, for example, methyl mercaptan, ethyl mercaptan, thiophenol, thiocresol, chlorothiophenol, dimethyl disulfide, diethyl disulfide and diphenyl disulfide.

The basic catalysts usable include alkali cyanide such as sodium cyanide and potassium cyanide, alkali hydroxide such as sodium hydroxide and potassium hydroxide, ammonia, and lower alkylamines which include dialkyl and trialkylamine, such as triethylamine and tributylamine.

In the invention, the addition of organic mercaptans and/or organic disulfides produces an improvement on the yield of diaminomaleonitrile, but does not take effect at all without a basic catalyst. This fact suggests that the basic catalyst may be the polymerization initiator, and the organic mercaptan and disulfide may be the polymerization regulator and, in addition, contribute the tetremerization of hydrogen cyanide.

The reaction of the invention takes place in the liquid phase. The liquid phase may be provided by a wide variety of organic solvents. The principal requirements for the solvents are that they be liquid under the conditions employed and remain inert to the reactant and product. The employable solvents are, for example, polar aprotic solvents such as dimethylformamide, dimethylsulfoxide, acetonitrile, propionitrile, n-butyronitrile, dimethylacetoamide the hexamethyl phosphoroamide. These polar aprotic solvents dissolve diaminomaleonitrile. The other organic solvents which are inert to the reactant and product, in other words, which are not aldehydes, carboxylic acids, ketones and alcohols, are also used in the invention. Such solvents include, for example, alkanes such as n-hexane, halogen-substituted aliphatic hydrocarbons such as chloroform, methylene chloride, carbon tetrachloride, ethylene dichloride and trichloroethylene, aromatic hydrocarbons such as benzene, toluene, xylene and ethylbenzene, and halogen-substituted aromatic hydrocarbons such as chlorobenzene and dichlorobenzene. These solvents do not dissolve diaminomaleonitrile (0.1% or less).

The amount of solvent is not critical in the invention, however it is uneconomical to use too much amount of solvent. The weight ratio of solvent to hydrogen cyanide is preferably 2 to 12.

The useful amount of basic catalyst and the amount of a cocatalyst. vary with the solvent, however they are generally 0.1 to 100 wt.% of an amount of solvent respectively, preferably 0.5 to 60 wt.%. The upper limit of the amount of a basic catalyst and a cocatalyst depends on the solubility thereof in a solvent. It is useless to use the catalysts in an amount over the solubility.

In case that the aforementioned polar aprotic solvents, which dissolve the product diaminomaleonitrile, are used as a solvent, the amount of both catalysts may be smaller. An amount of a basic catalyst may be 0.1 to 15 wt.% of an amount of a solvent, preferably 0.5 to 7 wt.%. An amount of a cocatalyst is 0.1 to 7 wt.% of an amount of a solvent, preferably 0.5 to 5 wt.%.

In the case of the aforementioned organic solvents other than said polar aprotic solvents, these solvents do not dissolve diaminomaleonitrile and a large amount of both catalysts is preferable. These are, for example, about 50wt.% of an amount of solvent respectively, however it depends on the solubility. Namely it is preferable to saturate the solvent with the catalysts.

In case that these solvents which do not dissolve the product are used as a solvent, though a large amount of the catalysts are used at a time, the separation of the product after the reaction is easy and the solvent dissolving the catalyst can be used repeatedly, so there is no disadvantage being caused by using a large amount of the catalysts.

The reaction of the invention is carried out at a temperature of −20° to 130°C, preferably 45° to 70°C. The reaction may take place at a temperature below −20°C, however longer reaction time is required. In case that the reaction temperature is above 130°C, it is apt to cause the over-polymerization (the production of by-products, higher polymer of hydrogen cyanide than tetramer).

According as the reaction temperature becomes higher and the concentration of the catalysts becomes higher, the rate of reaction increases. However, a high rate of reaction does not always cause a high yield, and when the rate of reaction is too fast a violent reaction occurs and the yield rather decreases.

Pressure is not a critical variable in the process.

When a basic catalyst or a cocatalyst except for mercaptans is liquid under the condition employed, such catalyst may be used as both catalyst and solvent and another solvent may be omitted. As a solvent, such catalyst belongs to the aforementioned solvent which does not dissolve diaminomaleonitrile. The catalyst usable as a solvent is, for example, alkylamines such as triethylamine, and dialkyldisulfides containing 2 to 6 of carbon atoms.

In order to separate the product from the resulting reaction mixture, when the solvent which dissolves the product is used, the solvent is distilled under atmospheric or reduced pressure after neutralizing a basic catalyst to remain the crude product, on the other hand, when the solvent which does not dissolve the product, filtration gives crude diaminomaleonitrile and the filtrate which includes a solvent and both catalysts may be circularly used for the reaction. The obtained crude diaminomaleonitrile as mentioned above may be purified by extraction process.

The extraction solvents include water, alcohols, ethylacetate, methylisobutylketone and the like.

According to the process of the invention, diaminomaleonitrile is obtained in a high yield such as 90 to 95% in a short reaction such as 1 hour.

The following examples are intended to aid in the understanding of the invention, and variations may be made by one skilled in the art without departing from the spirit and scope of the invention.

EXAMPLE 1

In a 200 ml flask were placed and sealed 110 g of dimethylformamide, 2.2g of thiophenol, 2.7g of sodium cyanide and 33.1g of hydrogen cyanide, and reacted at 60°C for 50 minutes with stirring. After the reaction was completed, the content of diaminomaleonitrile in the resulting reaction solution was analyzed by a ultraviolet spectrophotometer at wave-length of 296 m$\mu$.

As the results, it was identified to have obtained 30.5g of diaminomaleonitrile in a yield of 92% to the added hydrogen cyanide.

After decomposition of sodium cyanide in the resulting reaction solution with sulfuric acid, dimethylformamide was distilled away at a temperature of 100°C and at a pressure of 20 to 40 mmHg with a film-evaporator. The residue was twice washed with 100g of methylene chloride to remove thiophenol and changed material thereof, and then diaminomaleonitrile in the residue was extracted with 600g of ethyl acetate.

Evaporation to dryness of ethyl acetate gave 29.7g of pale yellow crystal diaminomaleonitrile. The purity of the product was 98.5% and the yield was 88% to hydrogen cyanide.

EXAMPLE 2

In a 200 ml flask were placed and sealed 110g of dimethylformamide, 2.2g of diphenyldisulfide, 2.7g of potassium cyanide and 33.1g of hydrogen cyanide, and reacted at 60°C for 60 minutes with stirring. After the reaction was completed, the resulting reaction solution was analyzed as in Example 1. As the result, it was identified to have obtained 31.4g of diaminomaleonitrile in a yield of 95% to hydrogen cyanide.

EXAMPLE 3

In a 200 ml flask were placed and sealed 100g of dimethylsulfoxide, 2.0g of p-chlorothiophenol, 2.0g of sodium hydroxide and 34.6g of hydrogen cyanide, and reacted at 60°C for 50 minutes with stirring. After the reaction was completed, the resulting reaction solution was analyzed as in Example 1. As the result, it was identified to have obtained 28.6g of diaminomaleonitrile in a yield of 88% to hydrogen cyanide.

EXAMPLE 4

In a 200 ml flask were placed and sealed 100g of hexamethylphosphortriamide, 2.0g of dibenzyldisulfide, 1.0g of sodium cyanide and 32.9g of hydrogen cyanide, and reacted at 60°C for 2.5 hours with stirring. After the reaction was completed, the resulting reaction solution was analyzed as Example 1. As the result, it was identified to have obtained 26.6g of diaminomaleonitrile in a yield of 81% to hydrogen cyanide.

EXAMPLE 5

In a 200 ml flask were placed and sealed 100g of dimethylsulfoxide, 2.0g of dimethyldisulfide, 2.0g of triethylamine and 28.4g of hydrogen cyanide, and reacted at 60°C for 5 hours with stirring. After the reaction was completed, the resulting reaction solution was analyzed as Example 1. As the result, it was identified to have obtained 19.3g of diaminomaleonitrile in a yield of 68% to hydrogen cyanide.

EXAMPLE 6

In a 200 ml flask were placed and sealed 89g of dimethylformamide, 1.8g of 2-mercaptobenzothiazole, 2.2g of sodium cyanide and 27.0g of hydrogen cyanide, and reacted at 60°C for 6 hours with stirring. After the reaction was completed, the resulting reaction solution was analyzed as in Example 1. As the result, it was identified to have obtained 19.2g of diaminomaleonitrile in a yield of 71% to hydrogen cyanide.

EXAMPLE 7

In a 200 ml flask were placed and sealed 89g of dimethylformamide, 1.8g of 3-mercapto-5-methyl-1,2,4-triazole, 2.2g of sodium cyanide and 27.0g of hydrogen cyanide, and reacted at 60°C for 6 hours with stirring. After the reaction was completed, the resulting reaction solution was analyzed as in Example 1. As the result, it was identified to have obtained 19.7g of diaminomaleonitrile in a yield of 73% to hydrogen cyanide.

EXAMPLE 8

In a 200 ml flask were placed and sealed 100g of dimethylformamide, 2g of diphenyldisulfide, 2.5g of triethylamine and 27.0g of hydrogen cyanide, and reacted at 65°C for 4 hours with stirring. After the reaction was completed, the resulting reaction solution was analyzed as in Example 1. As the result, it was identified to have obtained 20.5g of diaminomaleonitrile in a yield of 76% to hydrogen cyanide.

EXAMPLE 9

In a 200 ml flask were placed and sealed 100g of acetonitrile, 2.0g of diphenyldisulfide, 2.5g of triethylamine and 30.1g of hydrogen cyanide, and reacted at 50°C for 2.5 hours with stirring. After the reaction was completed, acetonitrile, triethylamine and unreacted hydrogen cyanide were distilled away to obtain 11.5g of residue. The residue was twice washed with 100g of methylene chloride and dried to obtain 9.5g of a crystal containing 8.7g of diaminomaleonitrile. The recovered hydrogen cyanide was 20.6g, and the yield of the product was 92% to the consumed hydrogen cyanide.

EXAMPLE 10

In a 200 ml flask were placed and sealed 100g of n-butyronitrile, 3g of thiophenol, 2.0g of triethylamine and 27.0g of hydrogen cyanide, and reacted at 70°C for 7 hours with stirring. After the reaction was completed, n-butyronitrile, triethylamine and unreacted hydrogen cyanide were distilled away to obtain 13.5g of residue. The residue was twice washed with 100g of toluene and dried to obtain 10.5g of a crystal containing 7.9g of diaminomaleonitrile. The recovered hydrogen cyanide was 16.5g, and the yield of the product was 75% to the consumed hydrogen cyanide.

EXAMPLE 11

1. To 100g of toluene placed in a 300 ml flask were dissolved 50g diphenyldisulfide and 50g of triethylamine. To the solution was charged and sealed 27.0g of hydrogen cyanide, and reacted at 50°C with stirring. Produced diaminomaleonitrile began to precipitate 20 minutes after starting the heating. The reaction was continued for 1 hour. After the reaction was completed, the precipitated diaminomaleonitrile was separated by filtration. The crude product was washed with 20g of toluene and dried to yield 16.4g of crude diaminomaleonitrile which had a purity of 76%.

The mother liquor including the toluene used for washing was 209g and it contained 2.25g of hydrogen cyanide. The yield of product was 50.4% to the consumed hydrogen cyanide.

2. To 209g of the above-mentioned mother liquor was added and sealed 27.0g of hydrogen cyanide. The mixture was heated at 78°C for 20 minutes. The precipitated product was separated by filtration and washed with 20g of toluene and dried to yield 27.9g of brown-black crude diaminomaleonitrile which had a purity of 83.2%.

The mother liquor including the toluene used for washing was 207g and it contained 3.91g of hydrogen cyanide.

The yield of the product was 91.5% to the consumed hydrogen cyanide.

The reaction was repeated similarly by recycling the mother liquor. The result was shown in the Table 1.

Table 1

| No. | Used mother liquor g. (contained HCN g.) | Added HCN g. | Temp. °C | Time min. | Crude product g. (purity %) | Yield to consumed HCN % |
|---|---|---|---|---|---|---|
| (3) | 207 (3.91) | 27.0 | 50 | 60 | 25.1 (82.1) | 72.8 |
| (4) | 205 (2.60) | 27.0 | 60 | 50 | 29.1 (81.4) | 85.6 |
| (5) | 205 (1.92) | 27.0 | 57 | 40 | 26.4 (78.5) | 78.3 |
| (6) | 203 (2.43) | 27.0 | 56 | 50 | 25.8 (80.8) | 78.8 |

EXAMPLE 12

1. To 100g of toluene placed in a 300 ml flask were dissolved 40g of diphenyldisulfide and 50g of triethylamine. To the solution was charged and sealed 27.0g of hydrogen cyanide, and reacted at 56°C with stirring. Produced diaminomaleonitrile began to precipitate 25 minutes after starting the heating. The reaction was continued for 1 hour, and then, the precipitated product was separated by filtration. The crude product was washed with 20g of xylene and dried to yield 18.1g of brown-black crude diaminomaleonitrile which had a purity of 75.6%.

The mother liquor including the xylene used for washing was 192g and it contained 2.32g of hydrogen cyanide. The yield of the product was 55.4% to the consumed hydrogen cyanide.

2. To 192g of the above-mentioned mother liquor was added and sealed 27.0g of hydrogen cyanide. The mixture was heated at 80°C for 25 minutes. The precipitated product was separated by filtration and washed with 20g of xylene and dried to yield 26.6g of brown-black crude diaminomaleonitrile which had a purity of 81.8%.

The mother liquor including the xylene used for washing was 197g and it contained 3.64g of hydrogen cyanide.

The yield of the product was 84.7% to the consumed hydrogen cyanide.

The reaction was repeated similarly by recycling the mother liquor. The result was shown in the Table 2.

Table 2

| No. | Used mother liquor g. (contained HCN g.) | Added HCN g. | Temp. °C | Time min. | Crude product g. (purity %) | Yield to consumed HCN % |
|---|---|---|---|---|---|---|
| (3) | 197 (3.64) | 27.0 | 59 | 60 | 26.5 (81.3) | 76.3 |
| (4) | 195 (2.46) | 27.0 | 61 | 50 | 25.8 (82.9) | 81.0 |
| (5) | 195 (3.03) | 27.0 | 58 | 40 | 24.4 (77.5) | 72.2 |
| (6) | 193 (3.85) | 27.0 | 56 | 50 | 23.4 (82.5) | 85.0 |

COMPARATIVE EXAMPLE 1

Example 1 was repeated without thiophenol in order to confirm the effect of the thiophenol. The reaction was continued till the yield amounted to the maximum. It took 6 hours. The resulting reaction solution contained 21.5g of diaminomaleonitrile. The yield was 60%. In addition, a higher yield than 60% to a consumed hydrogen cyanide was not attained on the way of the said reaction either.

We claim:

1. In a process for the production of diaminomaleonitrile by tetramerization of hydrogen cyanide in the presence of a basic catalyst selected from the group consisting of alkalimetal cyanide, alkalimetal hydroxide, ammonia and alkylamines, the improvement therein which comprises tetramerizing hydrogen cyanide in the liquid phase at a temperature in the range of −20° to 130°C for a time period of from about 20 minutes to about 7 hours, in the presence of at least one cocatalyst selected from the group consisting of:
   a. thiophenol, thionaphthol, benzylthiol, and the aforesaid thiols having at least one substituent selected from the group consisting of halogen, mercapto, and a lower alkyl,
   b. dialkyl disulfides containing 2 to 16 carbon atoms,
   c. diphenyl disulfide, dinaphthyl disulfide, benzyl disulfide and said disulfides having at least one substituent selected from the group consisting of halogen, mercapto and a lower alkyl.

2. A process according to claim 1 wherein the basic catalyst is an alkylamine and the liquid phase is provided by said basic catalyst.

3. A process according to claim 1 wherein the cocatalyst is selected from dialkyl disulfides containing 2 to 6 carbon atoms and the liquid phase is provided by said cocatalyst.

4. A process according to claim 1 wherein the liquid phase is provided by an organic solvent.

5. A process according to claim 4 wherein the organic solvent is a polar aprotic solvent.

6. A process according to claim 4 wherein the organic solvent is an inert organic solvent to which the solubility of diaminomaleonitrile is 0.1 wt.% or less.

7. A process according to claim 4 wherein the amounts of the catalyst and the cocatalyst are in the range of 0.1 to 100wt.% of an amount of solvent respectively.

8. A process according to claim 7 wherein the amounts of the catalyst and the cocatalyst are in the range of 0.5 to 60wt.% of an amount of solvent respectively.

9. A process according to claim 1 wherein the liquid phase is provided by the basic catalyst.

10. A process according to claim 1 wherein the liquid phase is provided by the cocatalyst.

11. A process according to claim 1 wherein the temperature is in the range of 45° to 70°C.

* * * * *